United States Patent
Oster et al.

(10) Patent No.: US 6,215,028 B1
(45) Date of Patent: *Apr. 10, 2001

(54) PROCESS FOR THE PREPARATION OF CYCLOHEXANONES

(75) Inventors: Bernd Oster, Hirschberg; Peter Mackert, Darmstadt; Detlef Pauluth, Ober-Ramstadt; Markus Wydra, Rödermark, all of (DE)

(73) Assignee: Merck Patent Gesellschaft mit (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/184,080

(22) Filed: Nov. 2, 1998

(30) Foreign Application Priority Data

Nov. 3, 1997 (DE) .............................. 197 48 441

(51) Int. Cl.$^7$ ..................................... C07C 45/62
(52) U.S. Cl. ......................... 568/362; 568/338; 568/364; 568/365
(58) Field of Search .................... 568/338, 362, 568/376, 364, 365

(56) References Cited

U.S. PATENT DOCUMENTS 3,933,916 * 1/1976 Lejeune et al. ................... 260/586 R
5,886,232 * 3/1999 Landscheidt et al. ............... 568/322

* cited by examiner

*Primary Examiner*—Sreeni Padmanabhan
(74) *Attorney, Agent, or Firm*—Millen, White, Zelano & Branigan, P.C.

(57) ABSTRACT

The invention relates to a process for the preparation of cyclohexanones from the corresponding phenols by partial hydrogenation, characterized in that the reaction mixture obtained by means of the hydrogenation is treated with sulfonating agents before the isolation of the cyclohexanone.

11 Claims, No Drawings

PROCESS FOR THE PREPARATION OF CYCLOHEXANONES

The invention relates to a process for the preparation of cyclohexanones from the corresponding phenols by partial hydrogenation, the reaction mixture obtained by hydrogenation being treated with sulfonating agents before isolation of the cyclohexanone.

Cyclohexanones are important intermediates or final products in industrial organic chemistry. Appropriately substituted derivatives are particularly valuable intermediates for the synthesis of highly purified final products or are themselves final products of this type for the electronics industry, such as, for example, liquid crystals, for plant protection, such as, for example, fungicides, insecticides, herbicides or pesticides, or for the production of pharmaceutically highly active substances. Cyclohexanones are furthermore used in the industrial synthesis of plastics such as polyamides or in the field of coating and colourant production. Production of the appropriate cyclohexanones on a large industrial scale necessitates preparation which is as economical and environmentally compatible as possible.

It is known that cyclohexanones can be prepared by partial hydrogenation of corresponding phenols. U.S. Pat. Nos. 2,829,166 and 3,076,810 teach the hydrogenation of phenol to cyclohexanone in the presence of a palladium catalyst. In Bull. Chem. Soc. Jpn., 65, 824–830 (1992) and Bull. Chem. Soc. Jpn., 65, 2955–2959 (1992), the reaction of phenols to cyclohexanones as a function of the solvent and of the nature of the catalyst is described. U.S. Pat. Nos. 4,537,704 and 4,614,831 disclose the preparation of cyclohexanone carboxylic acid esters. JP 03181438 teaches the preparation of 4-isopropylcyclohexanone by partial hydrogenation in the presence of aliphatic and aromatic hydrocarbons. JP 03109346 finally describes the preparation of cyclohexane-1,4-dione by partial hydrogenation of hydroquinone in mesitylene or methanol.

As a rule, however, substance mixtures which, besides the desired cyclohexanones also contain the corresponding cyclohexanols and the unreacted phenols, are formed in the partial hydrogenation of phenols to cyclohexanones. The expenditure for the isolation of the cyclohexanone from the reaction mixture is therefore crucial for the economical utilization of the process.

Industrially applicable methods for the isolation of the cyclohexanone from a reaction mixture which is obtained by the hydrogenation of a phenol are primarily distillation and/or crystallization.

Frequently, however, differences in the properties of the structurally very similar mixture components are only small, such that distillative separation of the reaction mixture is associated with very high expenditure and moreover accompanied by yield losses. In the case of solids, compounds having very low vapour pressures or, in the case of sensitive substances, distillation can generally not be employed without problems.

Crystallization, too, cannot generally be carried out as a method of mixture separation, since the hydrogenated products cyclohexanone and cyclohexanol as a rule have a lower tendency to crystallize than the phenols employed. The industrial preparation of cyclohexanones is therefore frequently not possible in this way.

The object on which the invention is based was to discover a process for the preparation of cyclohexanones which does not have the disadvantages mentioned.

It has now surprisingly been found that cyclohexanones can be obtained in very good yields and high purities by partially hydrogenating the corresponding phenols and treating the reaction mixture obtained by this means with sulfonating agents before isolation of the cyclohexanone.

The invention thus relates to a process for the preparation of cyclohexanones by partial hydrogenation of phenols, in particular a process for the preparation of cyclohexanones of the formula I

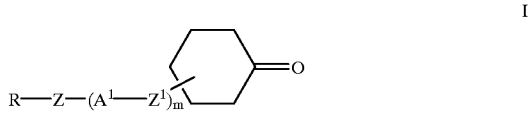

in which

R is one of the following chiral or achiral radicals:
H, F, —$CF_3$, —$OCF_3$, —$OCF_2CF_3$ or —$OCHFCF_3$, —$N(R^1)_2$, —$COOR^1$, —$CON(R^1)_2$, —CHO, a straight-chain or branched alkyd radical having 1 to 15 C atoms, which is unsubstituted, monosubstituted by —$CF_3$ or at least monosubstituted by fluorine, where in these radicals too one or more non-adjacent $CH_2$ groups can in each case independently of one another be replaced by —S—, —O—, —CO—, —CO—O—, —O—CO—, —O—CO—O— or

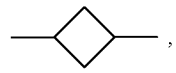

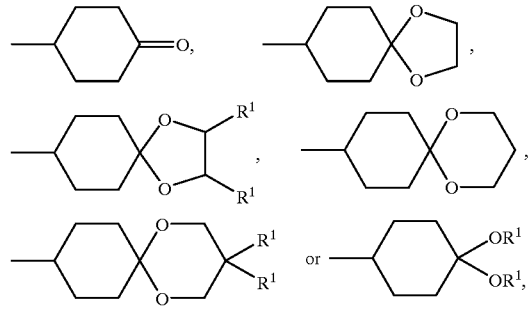

$R^1$ is an alkyl radical having 1 to 12 C atoms, $A^1$ is a
(a) cyclohexane-1,4-diyl radical, in which one or more non-adjacent $CH_2$ groups can also be replaced by —O— and/or —S—,
(b) 1,4-phenylene radical, in which one or two CH groups can also be replaced by N,
(c) radical from the group consisting of 2,6-dioxaborane-1,4-diyl, 1,4-bicyclo-[2.2.2]octylene, piperidine-1,4-diyl, naphthalene-2,6-diyl, decahydronaphthalene-2,6-diyl and 1,2,3,4-tetrahydronaphthalene-2,6-diyl,
where the radicals (a) and (b) can be substituted by one or more fluorine atoms, Z, $Z^1$ independently of one another are —$CH_2O$—, —$OCH_2$—, —CO—O—, —O—CO—, —$CH_2S$—, —$SCH_2$—, —$CH_2CH_2$— or a single bond m is 0, 1 or 2, by partial hydrogenation of the corresponding phenols of the formula II

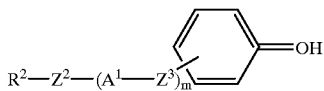
II in which

R² assumes the meaning of R and is additionally also

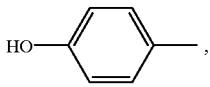

A¹ m have the meanings indicated for the formula I and Z², Z³ additionally the meaning indicated under Z and Z¹ are also —CH=CH— or —C≡C—, characterized in that the reaction mixture obtained by the partial hydrogenation is treated with sulfonating agents before the isolation of the cyclohexanone. Provided A¹ occurs a number of times in a compound of the formula I or II, it can assume the same or different meanings.

The same also applies to all other groups occurring a number of times.

The process according to the invention is particularly suitable for the preparation of intermediates for liquid crystal synthesis.

Preferably, those compounds of the formula II are used for the process in which the radical R²—Z²—(A¹—Z³)$_m$ is in the para-position to the phenolic hydroxyl group, as a result of which cyclohexanones of the formula I substituted in the 4-position are obtained.

For the sake of simplicity, in the following Phe is a 1,4-phenylene group, in which one or two CH groups can also be replaced by N, where a 1,4-phenylene group can also be substituted by one or two fluorine atoms, Cyc is a trans-cyclohexane-1,4-diyl radical and Dio is a trans-dioxane-1,4-diyl radical. W is the following group:

The preferred compounds prepared by the process according to the invention include those of the formulae Ia to Ir:

|                      |    |
|----------------------|----|
| W-Z-W                | Ia |
| W—A¹—Z¹—W            | Ib |
| R—A¹—Z¹—W            | Ic |
| R—A¹—Z¹—A¹—Z¹—W—     | Id |
| W—OOC—W              | Ie |
| W—CH₂CH₂—W           | If |
| W-Phe-W              | Ig |
| W-Cyc-W              | Ih |
| W-Dio-W              | Ii |
| W-Phe-OOC—W          | Ij |
| W-Cyc-CH₂CH₂—W       | Ik |
| R-Phe-W              | Il |
| R-Cyc-W              | Im |
| R-Dio-W              | In |
| R-Phe-OOC—W          | Io |
| R-Cyc-CH₂CH₂—W       | Ip |
| R-Cyc-Phe-W          | Iq |
| R—Z—W                | Ir |

In the preferred compounds of the formulae above and below, R is preferably an alkyl or alkoxy group having 1 to 10 C atoms, H, F, —CF₃, —OCF₃, —OCF₂CF₃, —N(R¹)₂, —COOR¹, —CON(R¹)₂, —CHO,

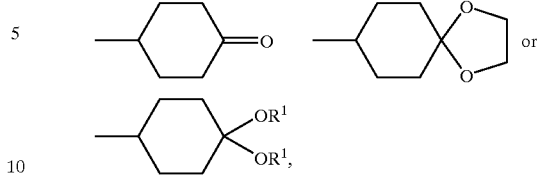

in particular a straight-chain alkyl or alkoxy group having 1 to 7 C atoms, H, F, —OCF₃, —COOR¹, —CON(R¹)₂,

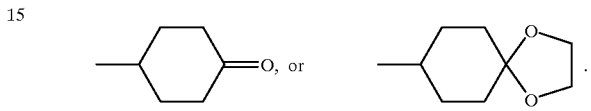

Those compounds of the formula II are in particular used for the process according to the invention in which m is 0 or 1. A particularly preferred compound which is employed as a starting material for the process according to the invention is 4,4'-dihydroxybiphenyl. By this means, 4,4'-dioxobicyclohexyl is obtained. A further preferred starting compound is 4,4'-dihydroxystilbene, from which 4(4'-oxocyclohexylethyl)cyclohexanone is obtained by the process according to the invention.

A¹ is preferably Cyc, or Phe. In the compounds of the formulae above and below, Phe is preferably a 1,4-phenylene group (Ph), a 1,4-phenylene group which is mono- or disubstituted by F (PheF), a pyrimidine-2,5-diyl (Pyr), a pyridine-2,5-diyl (Pyn), a pyrazine-3,6-diyl or a pyridazine-2,5-diyl group, particularly preferably Ph, PheF, Pyr or Pyn. Preferably, the compounds prepared by the process according to the invention contain no more than one 1,4-phenylene group in which one or two CH groups are replaced by N. Cyc is preferably a cyclohexane-1,4-diyl group. Compounds of the formula I are also particularly preferred in which at least one of the groups A¹ is a cyclohexane-1,4-diyl group which is substituted in the 1- or 4-position by F and the fluorine atom is in the axial position, i.e. the group A¹ has the following structure:

Compounds of the formula I and the subformulae below which contain a 2,3-difluoro-, 2,6-difluoro- or 3,5-difluoro-1,4-phenylene group are furthermore preferred.

The groups Z and Z¹ are preferably a single bond, —COO—, —OOC— or a —CH₂CH₂— group, in particular a single bond or a CH₂CH₂— group. Compounds of the formula I in which not more than one of the groups —CH₂CH₂—, —COO— or —OOC— occurs are preferred.

R¹ is preferably a straight-chain alkyl group having 1 to 5 C atoms, in particular methyl, ethyl, n-propyl or n-butyl.

If R is an alkyl group in which a CH₂ group (alkoxy or oxaalkyl) can also be replaced by an O atom, it can be straight-chain or branched. It preferably has 2, 3, 4, 5, 6, 7, 8, 9 or 12 C atoms and is accordingly preferably ethyl, propyl, butyl, pentyl, hexyl, heptyl, octyl, nonyl, decyl, ethoxy, propoxy, butoxy, pentoxy, hexoxy, heptoxy, octoxy, nonoxy or decoxy, furthermore also undecyl, dodecyl, undecoxy, dodecoxy, 2-oxapropyl (=2-methoxymethyl), 2-oxabutyl (=methoxyethyl) or 3-oxabutyl (=2-ethoxymethyl), 2-, 3- or 4-oxapentyl, 2-, 3-, 4- or 5-oxahexyl, 2-, 3-, 4-, 5- or 6-oxaheptyl. Hexyl, pentyl, butyl, n-butyl, propyl, i-propyl, methyl and ethyl, in particular propyl and pentyl, are particularly preferred: particularly preferred alkoxy groups are hexoxy, pentoxy, n-butoxy, propoxy, i-propoxy, methoxy and ethoxy, in particular ethoxy and n-butoxy. Compounds of the formula above and below having branched side groups R can be of importance. Branched groups of this type as a rule contain no more than two chain branchings. R is preferably a straight-chain group or a branched group having no more than one chain branching.

Preferred branched radicals are isopropyl, 2-butyl (=1-methylpropyl), isobutyl (=2-methylpropyl), tert-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl.

The radical R can also be an optically active organic radical having an asymmetric carbon atom. The asymmetric carbon atom is then preferably linked to two differently substituted C atoms, an H atom and a substituent selected from the group consisting of methyl or methoxy. The optically active organic radical R preferably has the formula $$—X'—Q'—\underset{\underset{Y'}{|}}{C^*H}—R^3$$

in which

X' is —O—, —S— or a single bond,

Q' is an alkyl group having 1 to 5 C atoms, in which a $CH_2$ group not linked to X' can also be replaced by —O—, or a single bond, Y' is F, —$CF_3$, methyl or methoxy and $R^3$ is an alkyl group having 1 to 5 C atoms other than Y', in which one or two non-adjacent $CH_2$ groups can also be replaced by —S— or —O—, X' is preferably a single bond, Q' is preferably —$CH_2$—, —$CH_2CH_2$—, —$CH_2CH_2CH_2$— or a single bond, particularly preferably a single bond, Y' is preferably —$CH_3$ or F, particularly preferably F, $R^3$ is preferably straight-chain or branched alkyl or alkoxy having 2 to 5, in particular 2 to 3, C atoms.

The process according to the invention is very particularly suitable for the prepartion of the cyclohexanones of the formulae I1 to I19:

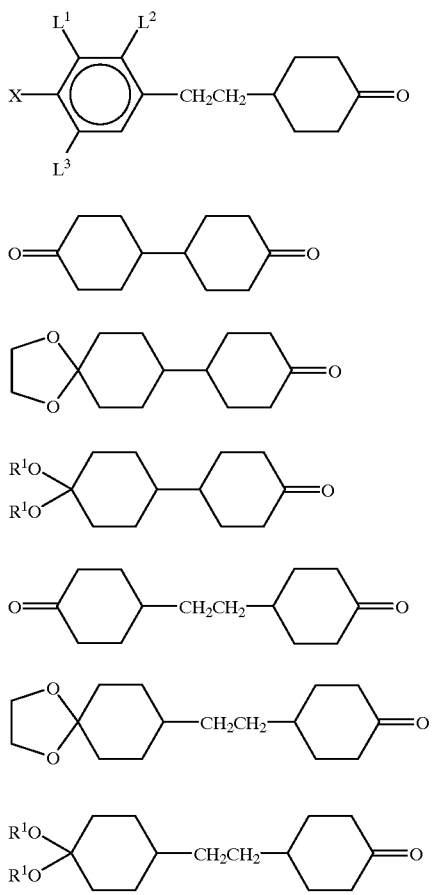

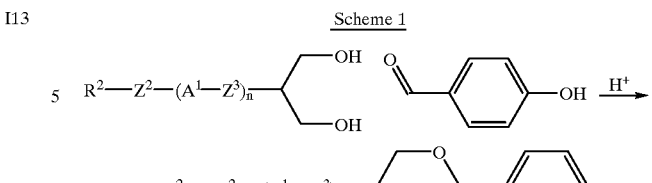

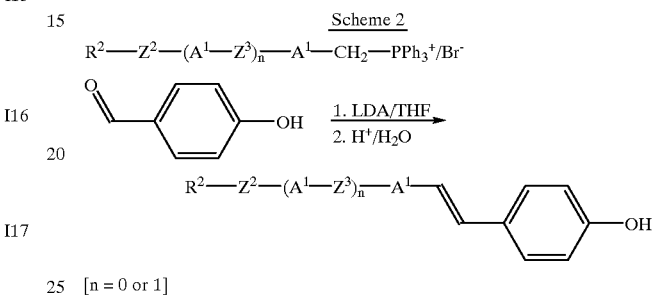

where
- $R^1$ has the meaning indicated above,
- $R^4$ is —N($R^1$)$_2$, —CON($R^1$)$_2$, a straight-chain alkyl radical having 1 to 12 C atoms, where one or more $CH_2$ groups in this radical can also be replaced by —O— or —CO— such that O atoms are not linked directly to one another,
- $L^1$, $L^2$, $L^3$ independently of one another are H or F and
- X is F, —$CF_3$, —$OCF_3$, —$OCF_2CF_3$ or —$OCHFCF_3$.

Very particularly preferred cyclohexanones which can be prepared by the process according to the invention are the compounds of the formulae I1, I2, I3, I4, I5, I7, I9, I13, I14, I15, I17 and I18.

The phenols needed as starting substances are either known or are prepared by methods known per se, such as are described in the literature (e.g. standard works such as Houben-Weyl, Methoden der organischen Chemie [Methods of Organic Chemistry], Georg-Thieme-Verlag, Stuttgart or Organikum, 17th Edition, VEB Deutscher Verlag der Wissenschaften, Berlin 1988), namely under reaction conditions which are known and suitable for the reactions mentioned. Thus the appropriate phenols can be prepared, for example, by alkali fusion of aromatic sulfonic acids, by boiling diazonium salt solutions or by oxidation of phenyl metal derivatives. However, use can also be made of variants which are known per se, but are not mentioned here in greater detail. Preferred phenols which serve as starting compounds for the process according to the invention can be obtained, for example, according to the following schemes:

The reaction procedure is simple, the phenol concerned first being partially hydrogenated in the usual way at temperatures from −20 to +250° C., preferably at −20 to +200° C., very particularly preferably at +20 to +200° C. and at normal or elevated hydrogen pressure, preferably at elevated hydrogen pressure. The hydrogenations are preferably carried out at a pressure of 1–50 bar, preferably at 2 to 10 bar. The length of the hydrogenation depends on the reaction conditions selected.

The nature of the catalyst to be employed in the hydrogenation is not critical per se. Customarily, the catalysts customary in organic chemistry are used (e.g. Organikum, 15th Ed., VEB, 1976, p. 359 ff or Houben-Weyl, Methoden der organischen Chemie [Methods of Organic Chemistry], Georg-Thieme-Verlag, Stuttgart). Catalysts with reduced hydrogenating activity can be used. Noble metal catalysts which contain platinum, rhodium or iridium in metallic or oxide form or a palladium catalyst are preferred. The catalysts can be used homogeneously or are used immobilized on a support such as, for example, activated carbon, alumina, silica, calcium carbonate or barium sulfate. Palladium catalysts which are applied to activated carbon (Pd/C) are particularly preferred.

A particularly suitable hydrogenation catalyst contains metallic palladium on a suitable support, preferably activated carbon, which has been doped with alkali metal or alkaline earth metal carbonate or hydroxide. The proportion of the alkali metal or alkaline earth metal doping to the total mass of the catalyst as a rule makes up 0.5 to 25% by weight, in particular 1 to 20% by weight. Doping is preferably carried out with alkali metal carbonate, in particular with sodium or potassium carbonate. The doping can be carried out, for example, by treating the palladium or the palladium/support mixture with alkali metal or alkaline earth metal carbonate in aqueous solution and then removing the water in vacuo.

As a rule, 0.001 to 0.5 parts, preferably 0.01 to 0.25 parts, of the catalyst are needed to 1 part of the phenol to be hydrogenated, where as a rule the active component of the catalyst, i.e. the transition metal, makes up approximately 1 to 30, preferably 2 to 15, % by weight of the total catalyst.

By means of hydrogenation under the conditions mentioned, in general only phenols or isolated triple or double bonds are hydrogenated. As a rule, benzene rings which do not carry any OH groups are not attacked.

Both the hydrogenation and also the subsequent sulfonation can be carried out in the melt or in solvents. It is preferably carried out in the presence of organic solvents. In general, the same solvent is used for the hydrogenation and the sulfonation in the process according to the invention.

Suitable solvents are in particular aromatic solvents, such as, for example, benzene, toluene, xylenes, mesitylene, anisole, phenetole or tetrahydronaphthalene. Furthermore, saturated hydrocarbons, such as cyclohexane, n-hexane or n-octane, esters such as methyl acetate, ethyl acetate, propyl acetate or butyl acetate, or ethers such as diethyl ether or methyl tert-butyl ether, tetrahydrofuran or dioxane can also be used. Alcohols, such as, for example, methanol, ethanol, n-propanol, i-propanol, n-butanol, i-butanol or tert-butanol are only suitable for the process according to the invention if they are removed after the hydrogenation and before the addition of the sulfonating agent and/or replaced by the non-alcoholic solvents or halogenated hydrocarbons mentioned, such as, for example, dichloromethane, trichloromethane, dichloroethylene or trichloroethylene. Preferred solvents for the process according to the invention are benzene, toluene, xylenes, mesitylene, anisole, phenetole or tetrahydronaphthalene, in particular toluene, o-xylene or mesitylene. Mixtures of the solvents mentioned can likewise be used.

The amount of solvent is not critical. In general 10 to 10,000 g of solvent can be added per mole of the phenol to be hydrogenated. Cosolvents such as tetramethylethylenediamine (TMEDA) or crown ethers, such as 18-crown-6, can be added to these solvents. Addition of substituted pyridines such as, for example, 3- or 4-dimethylaminopyridine is likewise possible.

Generally, solvents which are as anhydrous as possible should be used. While water which may be present does not interfere with the hydrogenation step of the process according to the invention, water which is present should be removed, for example by distillation, before the sulfonation takes place. Water present in the reaction mixture can only be neglected when using correspondingly larger amounts of the sulfonating agent.

The reaction mixture obtained by the hydrogenation of the phenol concerned, which, depending on the hydrogenation conditions and starting compound employed, contains different proportions of the cyclohexanone, of the corresponding cyclohexanol and/or of the unreacted phenol, is preferably treated with an amount of sulfonating agents which corresponds to the molar proportions of the cyclohexanol and phenol. Likewise, it is possible to employ an excess of sulfonating agents. In the treatment with sulfonating agents of the reaction mixture obtained by the partial hydrogenation, the hydroxyl group of the undesired cyclohexanol is converted into the corresponding sulfate or into the corresponding sulfuric acid hemiester. Depending on the sulfonating agent used, phenols can be converted into the respective sulfates or sulfuric acid hemiesters, but also into the corresponding phenolsulfonic acids.

It is a particular feature of the process according to the invention that the sulfonating agents react exclusively under the selected conditions with the components cyclohexanol and/or phenol contained in the reaction mixture obtained by means of the partial hydrogenation. A yield-restricting reaction of the cyclohexanone to give the corresponding α-ketosulfonic acids, such as is known for a number of ketones (e.g. Houben-Weyl, Methoden der organischen Chemie [Methods of Organic Chemistry], Vol. 9, p. 362 ff, 4th Edition, Georg-Thieme-Verlag, Stuttgart 1955), does not take place.

All known sulfonating agents are suitable for the process according to the invention. These are, for example, sulfuric acid, oleum, chlorosulfonic acid or chlorosulfonic acid-ether adducts, amidosulfonic acid, sulfur trioxide in undiluted form or diluted with nitrogen or air, sulfur trioxide-ether adducts or sulfur trioxide-nitrogen base adducts. Preferably, chlorosulfonic acid, sulfur trioxide in undiluted form or diluted with nitrogen or air or sulfur trioxide-nitrogen base adducts are employed. Sulfur trioxide-nitrogen base adducts are particularly preferred. These sulfur trioxide-nitrogen base adducts are commercially available or can be prepared by simple mixing together of the components. It may be advantageous to carry out the sulfonations with chlorosulfonic acid or chlorosulfonic acid-ether adducts, amidosulfonic acid, sulfur trioxide in undiluted form or diluted with nitrogen or air or sulfur trioxide-ether adducts in the presence of nitrogen bases.

The choice of the nitrogen base for the process according to the invention is not critical. Suitable nitrogen bases are, for example, nitrogen heterocycles, amines or amidines. Preferably, those nitrogen bases are employed in which no H atoms are bonded directly to an N atom. Preferred nitrogen bases are pyridines, pyrimidines, pyridazines, trialkylamines or dialkylarylamines, where the alkyl radicals in the trialkylamines and dialkylarylamines can be identical or different. Imidazole, pyridine, p-dimethylaminopyridine, m-dimethylaminopyridine, o-dimethylaminopyridine, pyrimidine, trimethylamine, triethylamine, tripropylamine, triisopropylamine, dimethylaniline, diethylaniline are particularly preferred. Pyridine, p-dimethylaminopyridine, m-dimethylaminopyridine, trimethylamine, triethylamine and dimethylaniline are very particularly preferred. Mixtures of the nitrogen bases mentioned can also be used.

The process according to the invention is advantageously carried out by adding the sulfonating agent at temperatures from −20° C. up to the boiling point of the least volatile component of the reaction mixture in each case, in particular between 0° C. and 80° C., with stirring to the reaction mixture obtained by means of the hydrogenation. The length of the sulfonation is in general from 0.1 to 10 hours, preferably 0.2 to 2 hours.

The process can also be carried out by adding the reaction mixture which was obtained by the hydrogenation to the sulfonating agent or to a solution of the sulfonating agent with stirring. The isolation of the cyclohexanone can be carried out in the usual manner following the sulfonation. For example, following the sulfonation a nitrogen base can optionally be added such that the sulfates and/or sulfonates formed can be removed by means of filtration. The filtration is preferably carried out through a layer of adsorbents. Adsorbents used in the process according to the invention are all known polar adsorbents which are suitable for adequately strongly binding the corresponding sulfates or sulfonates of the cyclohexanols and/or phenols chemically or physically. Examples of these are silica gel, alumina in neutral, acidic or basic form but also other customary media, such as, for example, molecular sieve or mixtures of adsorbents of the type mentioned.

By means of the filtration, the desired cyclohexanone is obtained directly or optionally after removal of the solvent in vacuo.

Likewise, it is possible in cases in which the desired cyclohexanone has a relatively high vapour pressure to subject the reaction mixture treated with sulfonating agents and nitrogen bases directly to distillation.

The process according to the invention can also be carried out by treating with water or an aqueous solution of a base, e.g. alkali metal or alkaline earth metal hydroxide, alkali metal or alkaline earth metal carbonate or alkali metal or alkaline earth metal hydrogencarbonates, preferably alkali metal or alkaline earth metal hydroxide, after the sulfonation of the reaction mixture and removing the sulfates and/or sulfonates of the cyclohexanols and/or phenols by washing. After drying the organic phase, the cyclohexanone is obtained directly or optionally after removal of the solvent. In a particularly preferred embodiment of the process according to the invention, a sulfur trioxide-nitrogen base adduct, in particular the sulfur trioxide-pyridine adduct, is added to the reaction mixture obtained by the partial hydrogenation with stirring as a solid or in solution. The process can preferably also be carried out by adding the reaction mixture which was obtained by the partial hydrogenation to a solution of nitrogen base and sulfur trioxide. In a further preferred embodiment, it is also possible to pass sulfur trioxide undiluted or diluted into a solution of the cyclohexanone, cyclohexanol and/or phenol and the nitrogen base with cooling. For the isolation of the cyclohexanone, in these preferred embodiments the sulfates and/or sulfonates formed are removed by filtration and the residue is optionally freed from the solvent. The filtration is preferably carried out through a layer of the abovementioned adsorbents.

It may be advantageous to add a distillation or crystallization after the removal of the sulfates and/or sulfonates of the cyclohexanols and/or phenols by filtration and the removal of the solvent.

The cyclohexanones of the formula I prepared by the process according to the invention from the phenols of the formula II are important intermediates or final products in organic industrial chemistry. Appropriately substituted derivatives are particularly valuable intermediates for the synthesis of highly refined final products, or are themselves final products of this type for the electronics industry, such as, for example, liquid crystals, for plant protection such as, for example, fungicides, insecticides, herbicides or pesticides, or for the preparation of pharmaceutically highly active substances.

Even without further embodiments, it is assumed that a person skilled in the art can utilize the above description to the widest possible extent. The preferred embodiments, however, are only to be interpreted as descriptive and in no way as limiting disclosure in any manner.

The following examples are intended to illustrate the invention without restricting it. If not stated otherwise, percentages are percentages by weight. All temperatures are indicated in degrees Celsius.

EXAMPLES

Preparation of the Hydrogenation Catalyst

A solution of 3 g of sodium carbonate in 100 ml of water is added with stirring to a suspension of 20 g of palladium on activated carbon (5% by weight) in 100 ml of deionized water. The mixture is stirred for a further 0.5–2 hours and the majority of the water is then removed by vacuum distillation on a rotary evaporator at 50° C. Sodium carbonate-doped catalyst pastes having a residual water moistness of 20–40% (w/w) result.

Example 1 trans-4-(4-n-Propylcyclohexyl)cyclohexanone

A soluton of 500 g of 4-(4-n-propylcyclohexyl)-phenol in 5 l of toluene is hydrogenated at a hydrogen pressure of 5 bar and 120° C. in the presence of 50 g of palladium on activated carbon (5% by weight). The reaction mixture is filtered and freed from water by azeotropic distillation. It is then treated with 110 g of pyridine sulfone (pyridine-sulfur trioxide complex), stirred at 50° C. for 1 hour and filtered using basic alumina. After removal of the solvent, 433 g (86% yield) of the trans-4-(4-n-propylcyclohexyl)cyclohexanone remain as a colourless solidified melt having a purity of 99.5% (GC).

Example 2

Ethyl cyclohexan-4-onecarboxylate

A solution of 50 g of ethyl 4-hydroxybenzoate in 500 ml of toluene is hydrogenated at 2.5 bar and 110° C. in the presence of palladium on activated carbon. The reaction mixture is filtered and freed from water by azeotropic distillation. It is then treated with 10 g of pyridine sulfone and stirred at 50° C. for 1 hour. After filtration with basic alumina and removal of the solvent, 49.6 g (97% yield) of ethyl cyclohexan-4-onecarboxylate having a purity of 94.1% (GC) remain.

Example 3

4,4,'-Bicyclohexanedione

A suspension of 50 g of 4,4'-biphenyldiol in 500 ml of toluene is hydrogenated at 5 bar and 125° C. in the presence of palladium on activated carbon. The reaction mixture is filtered and freed from water by azeotropic distillation. It is then treated with 29 g of pyridine sulfone and stirred at 50° C. for 1 hour. After filtration using basic alumina and removal of the solvent, 34.4 g (66% yield) of 4,4'-bicyclohexanedione remain as colourless crystals having a purity of 99.0% (GC).

Examples 4–7

Analogously to the preceding examples, the following cyclohexanones were obtained using the palladium catalyst doped with sodium carbonate:

| Sarting material | Product | Yield |
|---|---|---|
| (4) 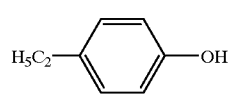 | 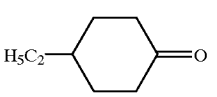 | 92% |

-continued

| Starting material | Product | Yield |
|---|---|---|
| (5) H₁₁C₅—〈cyclohexyl〉—〈phenyl〉—OH | H₁₁C₅—〈cyclohexyl〉—〈cyclohexyl〉=O | 92% |
| (6) 〈phenyl〉—〈phenyl〉—OH | 〈phenyl〉—〈cyclohexyl〉=O | 87% |
| (7) 〈phenyl〉—〈cyclohexyl〉—〈phenyl〉—OH | 〈phenyl〉—〈cyclohexyl〉—〈cyclohexyl〉=O | 82% |

The entire disclosure of all applications, patents and publications, cited above, and of corresponding German application No. 197 48 441.7, filed Nov. 3, 1997 is hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the preparation of cyclohexanones by partial hydrogenation of phenols, characterized in that any cyclohexanol and/or phenol present in the reaction mixture obtained by means of the partial hydrogenation of phenols is sulfonated with one or more sulfonating agents in the presence of nitrogen bases before the isolation of the cyclohexanone.

2. A process for the preparation of cyclohexanones by partial hydrogenation of phenols, which comprises the steps of treating a reaction mixture containing cyclohexanones obtained by means of the partial hydrogenation of phenols with an agent selected from the group consisting of chlorosulfonic acid, chlorosulfonic acid-ether adducts, amidosulfonic acid, sulfur trioxide, and sulfur trioxide-ether adducts in the presence of nitrogen bases before the isolation of the cyclohexanone.

3. A process according to claim 2 for the preparation of cyclohexanones of the formula I

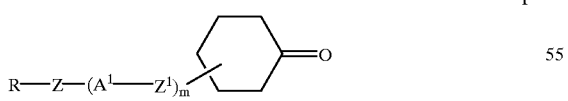

in which
R is one of the following chiral or achiral radicals:
H, F, —CF₃, —OCF₃, —OCF₂CF₃ or —OCHFCF₃, —N(R¹)₂, —COOR¹, —CON(R¹)₂, —CHO, a straight-chain or branched alkyl radical having 1 to 15 C atoms, which is unsubstituted, monosubstituted by —CF₃ or substituted by fluorine, in which one or more non-adjacent CH₂ groups can in each case, independently of one another, be replaced by —S—, —O—, —CO—, —CO—O—, —O—CO—, —O—CO—O or

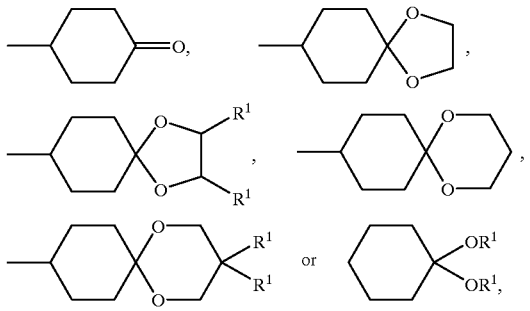

$R^1$ is an alkyl radical having 1 to 12 C atoms, $A^1$ is a
(a) cyclohexane-1,4-diyl radical, in which one or more non-adjacent CH₂ groups can also be replaced by —O— and/or —S—,
(b) 1,4-phenylene radical, in which one or two CH groups can also be replaced by N,
(c) radical from the group consisting of 2,6-dioxaborane-1,4-diyl, 1,4-bicyclo-[2.2.2]octylene, piperidine-1,4-diyl, naphthalene-2,6-diyl, decahydronaphthalene-2,6-diyl and 1,2,3,4-tetrahydronaphthalene-2,6-diyl, where the radicals (a) and (b) can be substituted by one or more fluorine atoms, $Z, Z^1$ independently of one another are —CH₂O—, —OCH₂—, —CO—O—, —O—CO—, —CH₂S—, —SCH₂—, —CH₂CH₂— or a single bond, m is 0, 1 or 2, by partial hydrogenation of the corresponding phenols of the formula II

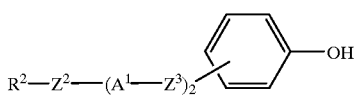

II in which

R² has the meaning of R of formula I and is additionally also

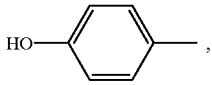

A¹, m have the meanings indicated for the formula I and Z²,Z³ have the meanings indicated for Z and Z¹ and are also —CH=CH— or —C≡C—.

4. A process according to claim 2, wherein the reaction mixture containing cyclohexanone additionally contains phenol and cyclohexanoyl, and is treated with an amount of chlorosulfonic acid, chlorosulfonic acid-ether adducts, amidosulfonic acid, sulfur trioxide or sulfur trioxide-ether adducts in the presence of nitrogen bases, corresponding to the molar proportions of the cyclohexanol and phenol in the reaction mixture.

5. A process according to claim 2, wherein the reaction mixture containing cyclohexanone is treated with chlorosulfonic acid, chlorosulfonic acid-ether adducts, amidosulfonic acid, sulfur trioxide or sulfur trioxide-ether adducts in the presence of nitrogen bases at temperatures of −20° C. up to the boiling point of the least volatile component of the reaction mixture in each case.

6. A process according to claim 2, wherein the reaction mixture containing cyclohexanone is treated with a sulfur trioxide-pyridine adduct before the isolation of the cyclohexanone.

7. A process according to claim 2, wherein the reaction mixture containing cyclohexanone and treated with chlorosulfonic acid, chlorosulfonic acid-ether adducts, amidosulfonic acid, or sulfur trioxide-ether adducts in the presence of nitrogen bases, is subjected to filtration.

8. A process according to claim 2, wherein the reaction mixture containing cyclohexanone is obtained by hydrogenation of phenols at temperatures between −20° C. and 200° C. and a hydrogen pressure from 1 to 50 bar.

9. A process according to claim 2, wherein the reaction mixture of cyclohexanone is obtained by the hydrogenation of the phenols in the presence of aromatic solvents and a palladium catalyst doped with alkali metal or alkaline earth metal carbonate or hydroxide.

10. A process according to claim 2, which prepares at least one compound of one of the formulae selected from the group consisting of formulae I1–I19:

I1

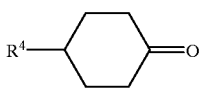

I2

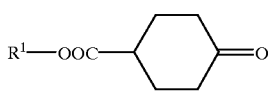

I3

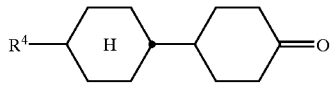

I4

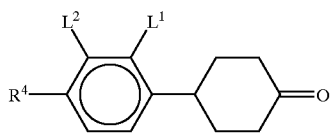

I5

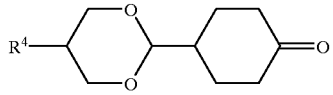

I6

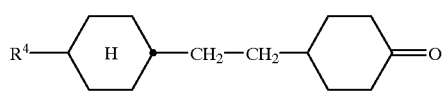

I7

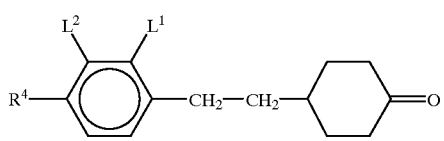

I8

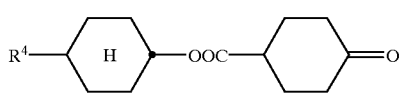

I9

I10

I11

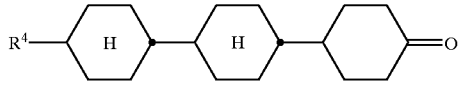

I12

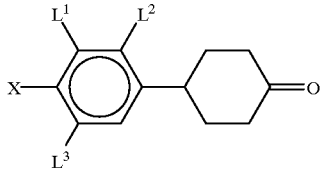

I13

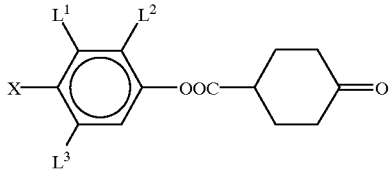

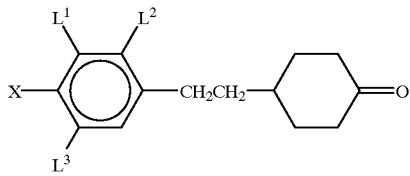

-continued

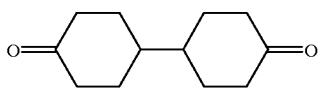
I14

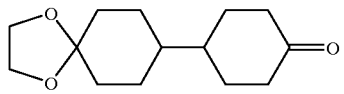
I15

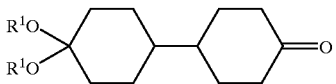
I16

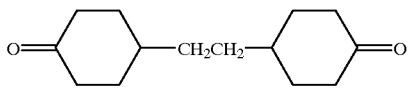
I17

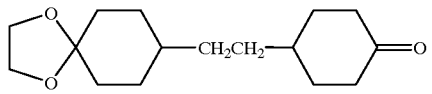
I18

-continued

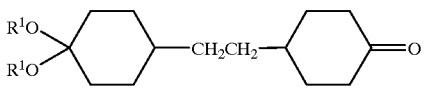
I19 where
R$^1$ is an alkyl radical having 1 to 12 C atoms
R$^4$ is —N(R$^1$)$_2$, a straight-chain alkyl radical having 1 to 12 C atoms, where one or more CH$_2$ groups in this radical can also be replaced by —O— or —CO— such that O atoms are not linked directly to one another,
L$^1$,L$^2$,L$^3$ independently of one another are H or F and
X is F, —CF$_3$, —OCF$_3$, —OCF$_2$CF$_3$ or —OCHFCF$_3$.

11. A process according to claim 2, wherein the reaction mixture containing cyclohexanone additionally contains cyclohexanol, phenol or both cyclohexanol and phenol and said reaction mixture is treated with a molar amount of chlorosulfonic acid, chlorosulfonic acid-ether adducts, amidosulfonic acid, sulfur trioxide or sulfur trioxide-ether adducts in excess of the molar amount of cyclohexanol and unreacted phenol within the reaction medium.

* * * * *